US009265974B2

(12) United States Patent
You et al.

(10) Patent No.: US 9,265,974 B2
(45) Date of Patent: Feb. 23, 2016

(54) APPARATUS, METHOD, AND COMPUTER-READABLE RECORDING MEDIUM FOR GENERATING TACTILE SENSATION THROUGH NON-INVASIVE BRAIN STIMULATION USING ULTRASONIC WAVES

(71) Applicants: Center Of Human-Centered Interaction For Coexistence, Seoul (KR); Korea Institute of Science and Technology, Seoul (KR); Catholic University Industry Academic Cooperation Foundation, Seoul (KR)

(72) Inventors: Bum Jae You, Seoul (KR); Sung On Lee, Seoul (KR); Yong An Chung, Seoul (KR)

(73) Assignees: Center Of Human-Centered Interaction For Coexistence, Seoul (KR); Korea Institute of Science and Technology, Seoul (KR); Catholic University Industry Academic Cooperation Foundation, Seoul (KR)

( * ) Notice: Subject to any disclaimer, the term of this patent is extended or adjusted under 35 U.S.C. 154(b) by 30 days.

(21) Appl. No.: 14/285,807

(22) Filed: May 23, 2014

(65) Prior Publication Data
US 2015/0251023 A1    Sep. 10, 2015

(30) Foreign Application Priority Data
Mar. 5, 2014    (KR) .................. 10-2014-0025996

(51) Int. Cl.
*A61N 7/00*    (2006.01)
*A61B 5/00*    (2006.01)
*G06F 1/00*    (2006.01)

(52) U.S. Cl.
CPC ................ *A61N 7/00* (2013.01); *A61B 5/4064* (2013.01); *G06F 1/00* (2013.01); *A61N 2007/0021* (2013.01); *A61N 2007/0026* (2013.01)

(58) Field of Classification Search
CPC .............. A61N 2007/0021; A61N 2007/0026; A61N 7/00
See application file for complete search history.

(56) References Cited

U.S. PATENT DOCUMENTS 6,536,440 B1 *  3/2003  Dawson ....................... 128/897
6,575,922 B1 *  6/2003  Fearnside et al. .............. 601/2
(Continued)

OTHER PUBLICATIONS

Legon W, Rowlands A, Opitz A, Sato TF, Tyler WJ (2012) Pulsed Ultrasound Differentially Stimulates Somatosensory Circuits in Humans as Indicated by EEG and fMRI. PLoS ONE 7(12): e51177. DOI:10.1371/journal.pone.0051177.*

(Continued)

*Primary Examiner* — Michael Rozanski
(74) *Attorney, Agent, or Firm* — Husch Blackwell LLP

(57) ABSTRACT

The present invention relates to an apparatus for creating a tactile sensation through non-invasive brain stimulation by using ultrasonic waves. The apparatus includes: an ultrasonic transducer module for inputting the ultrasonic waves to stimulate a specific part of the brain of a specified user non-invasively through at least one ultrasonic transducer unit; a compensating module for acquiring information on a range of tactile perception areas in the brain of the specified user and compensating properties of ultrasonic waves to be inputted to the specified user through the ultrasonic transducer unit by referring to the acquired information thereon; and an ultrasonic waves generating module for generating ultrasonic waves to be inputted to the specified user through the ultrasonic transducer unit by referring to a compensating value decided by the compensating module.

14 Claims, 6 Drawing Sheets

(56) References Cited

U.S. PATENT DOCUMENTS

| | | | |
|---|---|---|---|
| 6,584,357 B1* | 6/2003 | Dawson | 607/54 |
| 6,770,031 B2* | 8/2004 | Hynynen et al. | 600/437 |
| 6,978,179 B1* | 12/2005 | Flagg et al. | 607/45 |
| 7,283,861 B2* | 10/2007 | Bystritsky | 600/411 |
| 7,363,076 B2* | 4/2008 | Yun et al. | 607/3 |
| 7,699,768 B2* | 4/2010 | Kishawi et al. | 600/9 |
| 7,914,470 B2* | 3/2011 | Babaev | 601/2 |
| 7,974,845 B2* | 7/2011 | Spiridigliozzi et al. | 704/271 |
| 8,095,209 B2* | 1/2012 | Flaherty | 600/544 |
| 8,123,707 B2* | 2/2012 | Huckle et al. | 601/2 |
| 8,235,919 B2* | 8/2012 | Babaev | 601/2 |
| 8,560,041 B2* | 10/2013 | Flaherty et al. | 600/373 |
| 8,591,419 B2* | 11/2013 | Tyler | 600/439 |
| 8,855,775 B2* | 10/2014 | Leyde | 607/45 |
| 8,858,440 B2* | 10/2014 | Tyler | 600/439 |
| 8,884,746 B1* | 11/2014 | Cho et al. | 340/407.1 |
| 2011/0130615 A1* | 6/2011 | Mishelevich | 600/9 |
| 2011/0178441 A1* | 7/2011 | Tyler | 601/2 |
| 2013/0338526 A1* | 12/2013 | Howard | 600/544 |
| 2014/0148872 A1* | 5/2014 | Goldwasser et al. | 607/45 |
| 2014/0211593 A1* | 7/2014 | Tyler et al. | 367/137 |
| 2014/0330335 A1* | 11/2014 | Errico et al. | 607/45 |

OTHER PUBLICATIONS

Legon et al., Transcranial focused ultrasound modulates the activity of primary somatosensory cortex in humans, Nature Neuroscience, vol. 17, No. 2, Feb. 2014.*

Tufail et al., Ultrasonic neuromodulation by brain stimulation with transcranial ultrasound, Nature Protocols, vol. 6, No. 9, p. 1453 (2011).*

Tyler WJ, Tufail Y, Finsterwald M, Tauchmann ML, Olson EJ, et al. (2008) Remote Excitation of Neuronal Circuits Using Low-Intensity, Low-Frequency Ultrasound. PLoS ONE 3(10): e3511. doi:10.1371/journal.pone.0003511.*

* cited by examiner

APPARATUS, METHOD, AND COMPUTER-READABLE RECORDING MEDIUM FOR GENERATING TACTILE SENSATION THROUGH NON-INVASIVE BRAIN STIMULATION USING ULTRASONIC WAVES

CROSS REFERENCE TO RELATED APPLICATION

This application claims priority to and incorporates herein by reference all disclosure in Korean Patent Application No. 10-2014-0025996 filed Mar. 5, 2014.

FIELD OF THE INVENTION

The present invention relates to an apparatus, a method, and a computer-readable medium for generating a tactile sensation through brain stimulation; and more particularly, to the apparatus, the method, and the computer-readable medium for generating the tactile sensation desired by each individual accurately through non-invasive brain stimulation in use of ultrasonic waves by compensating properties of the ultrasonic waves in precise consideration of attributes of brains by respective individuals.

BACKGROUND OF THE INVENTION

Just like social networking services on the Internet, the real world and the virtual world are getting integrated. Now, communications are made in center of SMS text messages and videos, but attempts to communicate various senses to make people at a remote place feel as if they were together with each other in more reality have been achieved. In particular, attempts to deliver the tactile sensation, which is a very important sense for people just like visual and auditory senses, to remote places and feel the sense thereat have been made.

To send a user a feeling as if the user touched a virtual object or send the user at a remote place the feeling when a robot or person touches the object, a lot of haptic apparatuses for sending a tactile sensation and a force feedback to hands and arms of people have been developed. Recently, as actuators have been more compact and the performance of computers has been improved, a lot of developments have been made, but still they cannot send enough senses. In addition, since such systems with a plenty of mechanical units are still big and heavy for general users, they are used by experts only in a special application field.

In particular, to deliver a tactile sensation of a fingertip, approaches have been suggested by using following methods: a method for using electro-active polymers which implements a tactile display by using the expansion of polymers by ion exchange and also has an advantage of implementing it flexibly, but mostly has small driving power or requires driving voltages of several kilovolts depending on materials; a method for using piezoelectric materials which may cause greater force, but makes a device be thick and difficult to be bent; a magnetic driving method which has less force, and makes a device be thick and difficult to be bent; a pneumatic method which may cause a force to be great and flexible but has a disadvantage of causing a system to be larger and more complicated because respective pneumatic lines must be connected to arrays to actuate them, etc. However, such methods have not been commercialized yet due to limitations on size, weight, performance of delivering senses, etc. Such apparatuses must be put on a hand, and this, particularly, makes the user feel uncomfortable and drops a sense of immersion when the information on the tactile sensation is transmitted with the visual information.

As one of the methods for overcoming such problems, Sony Corporation suggested a method for stimulating a neural cortex by using ultrasonic waves in the U.S. Pat. No. 6,536,440 B1 (granted on Mar. 25, 2003). But the conventional Patent technology merely suggests an apparatus for generating ultrasonic waves with a double structure to form a variety of patterns, and the possibility of delivering visual information as such an example.

SUMMARY OF THE INVENTION

It is an object of the present invention to provide an apparatus for generating a tactile sensation through non-invasive brain stimulation that can stimulate a desired location of the brain accurately not only by predicting a reflection and a refraction phenomena arising from the ultrasonic waves passing through the skull of a user but also by considering characteristics of tactile perception areas of the user's brain while adjusting strength, frequency, and interval of ultrasonic waves to generate various senses of touch such as senses of pressure, vibration, temperature, sliding, etc.

It is further an object of the present invention to provide an apparatus for generating a tactile sensation through non-invasive brain stimulation in a form of headgear such as a helmet or a headset that can induce a tactile sensation or emotion and relieve abnormal human movements, e.g., tremors of hands, and spasms caused by Alzheimer's disease, by stimulating a specific area of the brain.

In accordance with one aspect of the present invention, there is provided an apparatus for creating a tactile sensation through non-invasive brain stimulation by using ultrasonic waves, including: an ultrasonic transducer module for inputting the ultrasonic waves to stimulate a specific part of the brain of a specified user non-invasively through at least one ultrasonic transducer unit; a compensating module for acquiring information on a range of tactile perception areas in the brain of the specified user and compensating properties of ultrasonic waves to be inputted to the specified user through the ultrasonic transducer unit by referring to the acquired information thereon; and an ultrasonic waves generating module for generating ultrasonic waves to be inputted to the specified user through the ultrasonic transducer unit by referring to a compensating value decided by the compensating module.

In accordance with another aspect of the present invention, there is provided a method for creating a tactile sensation through non-invasive brain stimulation by using ultrasonic waves, including the steps of: (a) acquiring information on a range of tactile perception areas in the brain of a specified user as information required to stimulate a specific part of the brain of the specified user non-invasively through at least one ultrasonic transducer unit included in an ultrasonic transducer module; (b) compensating properties of the ultrasonic waves to be inputted to the specified user through the ultrasonic transducer unit by referring to the acquired information on the range of the tactile perception areas in the brain of the specified user; and (c) generating ultrasonic waves whose attributes have been compensated and allowing them to be inputted to the specified user through the ultrasonic transducer unit.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

Figure 1:
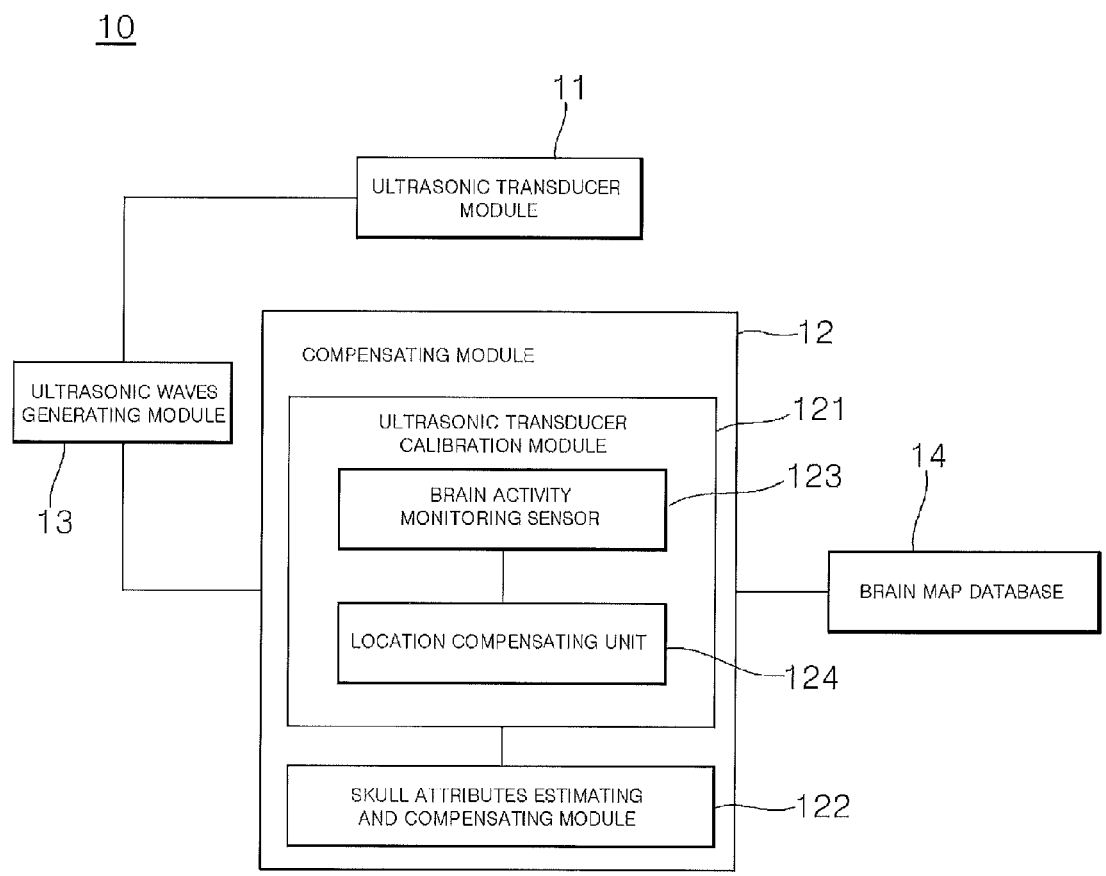
FIG. 1 shows a configuration of an apparatus for generating a tactile sensation through non-invasive brain stimulation by using ultrasonic waves in accordance with the present invention.

The detailed description of the present invention illustrates specific embodiments in which the present invention can be performed with reference to the attached drawings.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the present invention, although different, are not necessarily mutually exclusive. For example, a particular feature, structure, or characteristic described herein in connection with one embodiment may be implemented within other embodiments without departing from the spirit and scope of the present invention. In addition, it is to be understood that the location or arrangement of individual elements within each disclosed embodiment may be modified without departing from the spirit and scope of the present invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views.

To allow those skilled in the art to the present invention to be carried out easily, the example embodiments of the present invention by referring to attached diagrams will be explained in detail as follows:

FIG. 1 shows a configuration of an apparatus for generating a tactile sensation through non-invasive brain stimulation by using ultrasonic waves in accordance with the present invention.

Figure 2:
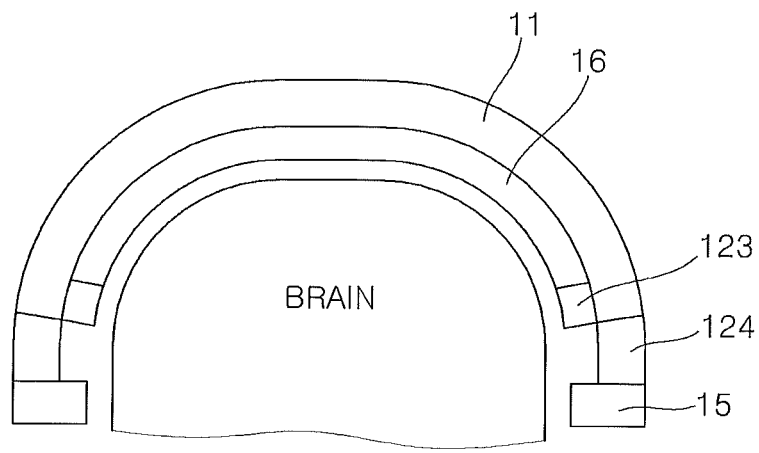
FIG. 2 illustrates the apparatus for generating the tactile sensation through the non-invasive brain stimulation in accordance with an example embodiment of the present invention.

FIG. 2 illustrates the apparatus for generating the tactile sensation through the non-invasive brain stimulation in accordance with one example embodiment of the present invention.

By referring to FIG. 1, an apparatus 10 for generating a tactile sensation in accordance with the present invention includes an ultrasonic transducer module 11, a compensating module 12, an ultrasonic waves generating module 13, brain map database 14, and so forth. For reference, a reference number 15 illustrated in FIG. 2 indicates a support fixture and a reference number 16 means a medium for transmitting the ultrasonic waves.

More specifically, the ultrasonic transducer module 11 performs a function of inputting, to a specified user, ultrasonic waves to stimulate a specific part of his or her brain non-invasively through one or more ultrasonic transducer units. The ultrasonic transducer module 11 may include only one transducer unit or a transducer array made of several transducer units.

The compensating module 12 performs a function of acquiring information on a range of tactile perception areas in the brain of the specified user (where the range means at least some pieces of information on accurate location, length, size, etc. of the areas on the cortex of the brain on which certain tactile sensations are perceived), and compensating properties of ultrasonic waves to be inputted to the specified user through the ultrasonic transducer unit(s) by referring to the acquired information on the range of the tactile perception areas in the brain of the specified user.

More specifically, the compensating module 12 acquires the information on the range of the tactile perception areas in the brain of the specified user by referring to a first tactile perception location in the tactile perception areas in the brain that perceives stimulation, if being inputted, to a first body part of the specified user, and a second tactile perception location therein that perceives stimulation, if being inputted, to a second body part and compensates properties of the ultrasonic waves to be inputted to the specified user through the ultrasonic transducer module 11 by referring to the acquired information on the range of the tactile perception areas in the brain of the specified user. At the time, it compensates the properties of the ultrasonic waves to be inputted to the specified user by referring to a path from the first tactile perception location to the second tactile perception location along the tactile perception areas in the brain of the specified user. Herein, the first body part could be a first finger of one hand of the specified user and the second body part could be a second finger thereof, but they are not limited only to these.

For doing this, the compensating module 12 may include an ultrasonic transducer calibration module 121, which may perform a function of compensating the properties of the ultrasonic waves to adjust a location on the brain of the specified user on which the ultrasonic waves focus by referring to the range of the tactile perception areas of the specified user.

To put it concretely, the ultrasonic transducer calibration module 121 may include a brain activity monitoring sensor 123 and a location compensating unit 124.

The brain activity monitoring sensor 123 may acquire information on the range of a specific tactile perception area, which is used to feel a certain tactile sensation, among all the tactile perception areas in the brain of the specified user. To do this, the brain activity monitoring sensor 123 acquires information on a first tactile perception location, that can perceive the stimulation on a first body part of the specified user, among the entire tactile perception area in the brain and a second tactile perception location, that can perceive the stimulation on a second body part thereof, among the entire tactile perception area in the brain, and then acquires information on the range of the tactile perception areas in the brain of the specified user by referring to the information on the first and the second tactile perception locations. This will be additionally explained by referring to FIG. 5 below. The brain activity monitoring sensor 123 may perform a function of getting the information on the range of the specific tactile perception areas more accurately by monitoring even the size of the brain that changes depending on emotions and mental states of the specified user and then deciding the accurate size of the brain at the present status.

Figure 3:
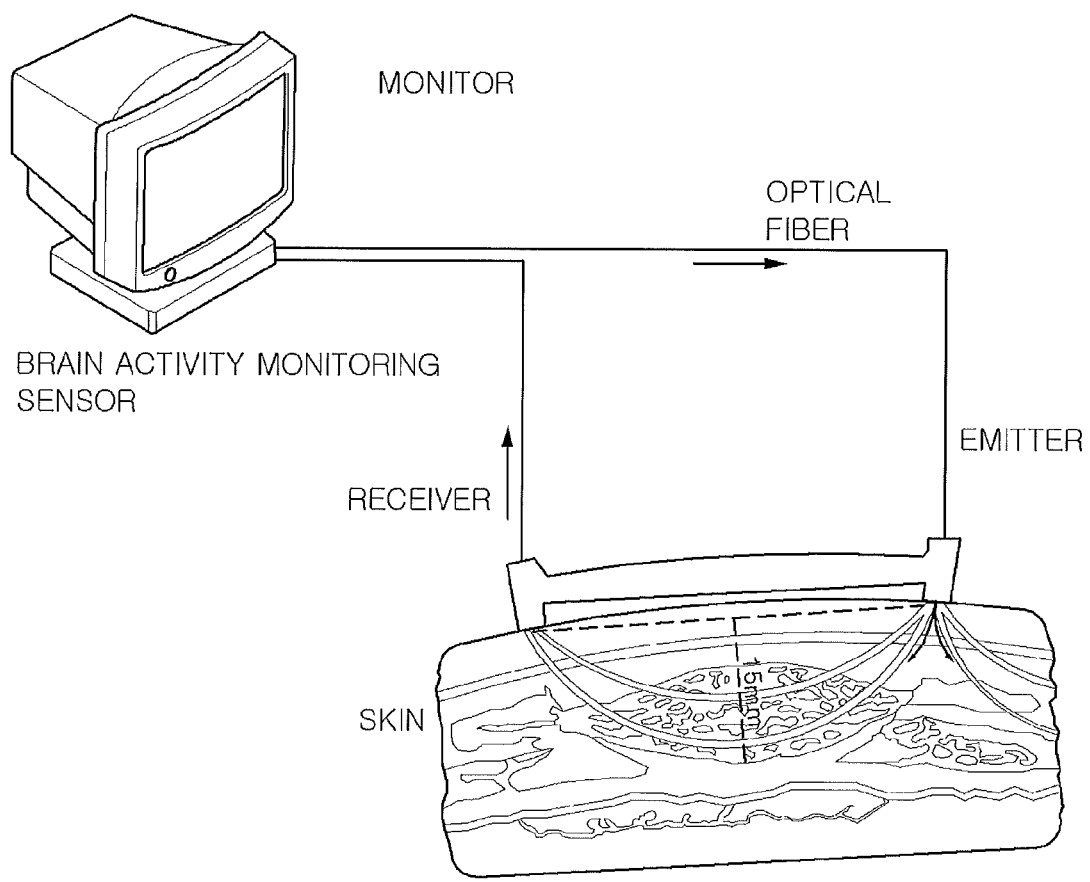
FIG. 3 represents the operation of a brain activity monitoring sensor.

FIG. 3 represents the operation of the brain activity monitoring sensor.

Figure 4:
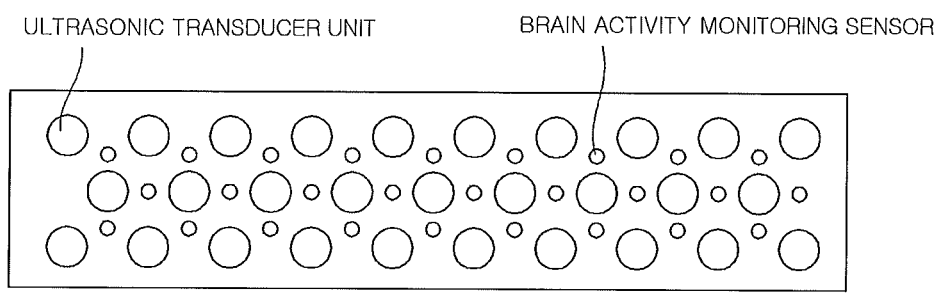
FIG. 4 illustrates a state of combining an ultrasonic transducer module and the brain activity monitoring sensor in accordance with an example embodiment of the present invention.

By referring to FIG. 3, as the brain activity monitoring sensor 123, a near infrared spectroscopic sensor (NIRS) or similar sensors may be used. As illustrated in FIG. 3, the NIRS measures oxygen consumption of the brain by including at least one emitter and at least one receiver. Herein, multiple emitters and receivers may be included to increase location resolution. The brain activity monitoring sensor 123 may be used independently from the ultrasonic transducer module 11. As illustrated in FIG. 2, it may be freely placed among or around individual ultrasonic transducers of the ultrasonic transducer module 11. As shown in FIG. 2, the ultrasonic transducer module 11, if being manufactured in a large hemispheric shape, may complete sensing by installing multiple monitoring sensors 123 on a separate track which allows a linear motion in X and Y directions, move the monitoring sensors 123 to an edge part, and then adjust ultrasonic transducers which are possible to move in directions X, Y, and Z before placing them to appropriate places to perform the brain stimulation. If several ultrasonic transducer units are used, the brain activity monitoring sensors 123 are placed among ultrasonic transducer units, making the ultrasonic transducer units and the brain activity monitoring sensors 123 as one module, and using them while moving in directions X, Y, and Z (Refer to FIG. 4). Of course, the brain activity monitoring sensor 123 could be also placed as shown in FIG. 2.

The emitter of the brain activity monitoring sensor 123 sends out light by making contact with scalp and the receiver thereof measures wavelength change by receiving the light reflected from the brain. At the time, mainly the change of the cortex is measured because the light from the emitter cannot be transmitted deeply.

Figure 5:
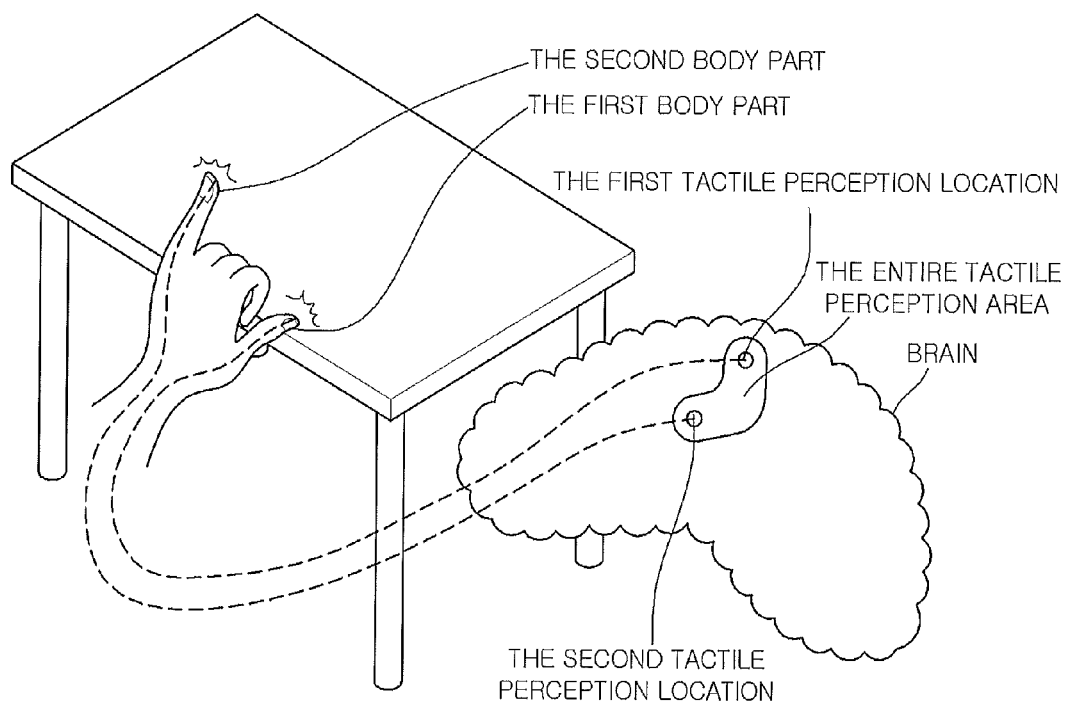
FIG. 5 depicts an example of acquiring information on the size of tactile perception areas in a brain by using fingers in accordance with an example embodiment of the present invention.

FIG. 5 depicts an example of the brain activity monitoring sensor 123 which acquires information on the range of the tactile perception areas in the brain by using fingers.

Because the brain size of every person is different and even the range of the tactile perception areas is slightly different, a location of a cortical area that responds to a tactile stimulation becomes slightly different. Accordingly, an initial location of the ultrasonic transducer module 11 becomes adjusted to the location where ultrasonic stimulation is easy by observing the activity of the brain that responds to the stimulation to two body parts of the user (e.g., two fingertips or two tiptoes). In addition, because the locations and sizes of the tactile areas of brains by individual persons are different and the size of a person's brain may be changed depending on his or her emotion and mental status, the information on the range of the tactile perception areas in the brain by respective body parts is obtained by using the information detected by the brain activity monitoring sensor 123 through calibration, i.e., normalization to the full length (or size) of the tactile areas of the cortex. Accordingly, stimulation locations of the body parts may be adjusted minutely.

FIG. 5 illustrates an example of using the first finger (e.g., a thumb) and the second finger (e.g., a small finger) as the first and second body parts of the user to stimulate. As illustrated in FIG. 5, after stimulation is given by facing the big thumbs and small fingers of both hands with each other to press or touch each other or by tapping the thumb and the small finger repeatedly on a hard place such as a desk, the locations responding to the stimulation can be detected through the brain activity monitoring sensor 123 and information on the range of the areas which take charge of tactile perception of the thumb and the small finger, respectively, can be obtained in the whole tactile area of the cortex by using the information on the detected locations.

By referring to FIG. 1 again, the location compensating unit 124 in the ultrasonic transducer calibration module 121 performs a function of adjusting the location of the focal point of an ultrasonic transducer module 11 which is focused on the brain of the specified user by referring to the information on the accurate size of the brain at the current status and/or the information on the range of the specific tactile perception area that is acquired through the brain activity monitoring sensor 123.

When the location on the brain of the user on which the ultrasonic waves to be inputted to the user are focused is adjusted, the location compensating unit 124, at the time, may adjust the location at the status of having three degrees of freedom, e.g., axes x, y, and z, all of which may be adjusted with software. Otherwise, two of three degrees of freedom may be adjusted with hardware and the other one may be adjusted with software. A method for adjusting degrees of freedom with software is to adjust the properties of the ultrasonic waves, e.g., a strength, a frequency, a phase difference, a launch angle, etc. of the ultrasonic waves inputted to the user through the ultrasonic transducer unit, while a method for adjusting them with hardware is to adjust the location of the ultrasonic transducer module 11 physically on the head, i.e., the skull, of the user. For example, a location and a depth where the ultrasonic waves are focused may be adjusted by adjusting the strength, the frequency, the phase difference, the launch angle, etc. of the ultrasonic transducer units, if all the three degrees of freedom are adjusted with software; and the location of the directions x and y may be adjusted through the move of the physical location of the ultrasonic transducer module 11 and that of the direction z, i.e., the direction of depth, through the adjustment of the strength or the phase difference of the ultrasonic waves with software, if two degrees of freedom are adjusted with hardware while one degree of freedom is with software.

As explained above, since the ultrasonic transducer calibration module 121 includes the brain activity monitoring sensor 123 and/or the location compensating unit 124, the ultrasonic transducer calibration module 121 may perform a function of compensating the properties of the ultrasonic waves or adjusting the physical location of the ultrasonic transducer module 11 on the brain of the specified user to adjust the location of the brain on which the ultrasonic waves are focused by referring to the range of the tactile perception areas.

The compensating module 12 may additionally include not only the ultrasonic transducer calibration module 121 but also a skull attributes estimating and compensating module 122, if necessary.

More specifically, the skull attributes estimating and compensating module 122 may perform a function of compensating the properties of the ultrasonic waves to be inputted to the user through the ultrasonic transducer module 11 by referring to the thickness of the skull of the brain of the user and the thickness of scalp or fat layer thereof.

Just as having different sizes of their brains and different sizes and locations of the tactile perception areas, individual persons have different skulls and scalps and also different internal layers of fat in thickness. Further, skins of skull, and transmission properties of the ultrasonic waves, e.g., ultrasonic refraction index of skulls, are different by individual persons. Accordingly, the skull attributes estimating and compensating module 122 performs a function of compensating the properties of the ultrasonic waves to be inputted to the user through the ultrasonic transducer module 11 to make the ultrasonic waves focused on the desired specific part of the brain by referring to the properties of the transmission of the ultrasonic waves that include attributes of reflection and/or refraction at the skull of the brain of the user. The skull attributes estimating and compensating module 122 decides the data recorded on the brain map database 14 as a reference value and then compensates the properties of the ultrasonic waves to be inputted to the user through the ultrasonic transducer module 11 by referring to the properties of the transmission which is different by individual users.

By referring to FIG. 1 again, the ultrasonic waves generating module 13 generates the ultrasonic waves to be inputted to the user through the ultrasonic transducer unit by referring to the compensation value decided by the compensating module 12. In other words, it performs a function of generating the ultrasonic waves by referring to the strength, the frequency, the phase difference, etc. of the ultrasonic waves decided by the compensating module 12.

In short, according to the aforementioned explanation, it could be introduced that the ultrasonic waves generating module 13 may generate ultrasonic waves by compensating the properties of the ultrasonic waves based on information on the size of the brain changed depending on the emotion or mental state of the user and the information on the range of the tactile perception areas decided by the brain activity monitoring sensor 123 and/or and it also could be introduced that the ultrasonic waves generating module 13 may generate ultrasonic waves by compensating the properties of the ultrasonic waves by referring to not only information acquired by the brain activity monitoring sensor 123 but also thickness of the skulls of individual users measured by the skull attributes estimating and compensating module 122.

The brain map database 14 is a database that stores data of the brains acquired from multiple users and also information on locations of the brains to be stimulated to deliver various senses of touch and the properties of the ultrasonic waves to transmit such senses of touch. In the brain map database 14, map data for the tactile perception areas in the brains of persons in general can be stored. In addition, the properties of the ultrasonic waves to transmit a tactile sensation stored in the brain map database 14 include information on a strength, a frequency, a phase difference, etc. of ultrasonic pulses.

Individual differences among persons exist, but the general configurations of the cortexes that respond to tactile stimulation can be seen as similar to one another. Besides, patterns responding to various senses of touch such as vibration and senses of pressure, texture, and temperature and pain are alike. Accordingly, information on the locations for the general tactile response areas of the cortexes of such persons in a similar shape, and patterns responding to various senses of touch is stored in the brain map database 14, in addition to the information on strengths, intervals, frequencies and phases of ultrasonic pulses to transmit corresponding senses of touch. If the database on a somatosensory brain map is implemented by gathering information on a location, a strength, a frequency, etc. of ultrasonic stimulation standardized depending on senses of touch, the already known somatosensory brain map database could also be used as it is. A support fixture 15 performs a function of fixing the apparatus 10 for generating the tactile sensation on the head of the user and supporting it directly or indirectly with the brain activity monitoring sensor 123, the location compensating unit 124, etc.

A medium 16 for transmitting the ultrasonic waves is made of a material for making the ultrasonic waves pass even through the scalp of the user without any reduction of the ultrasonic waves emitted from the ultrasonic transducer module 11 and it is attached under the ultrasonic transducer module 11 in prescribed thickness. The medium 16 for transmitting the ultrasonic waves could be made of ultrasound transmission gel used for ultrasonic testing or a water bag with degassed water.

When a location of a focus for stimulation on the brain and a type of tactile stimulation are selected through such configuration, a strength, a phase difference between pulses, a frequency, etc. of the ultrasonic waves and a physical location of the ultrasonic transducer module are adjusted to give stimulation to the brain. As stimulation is put to the specific area, the brain of the user comes to perceive a certain desired tactile sensation.

Figure 6:
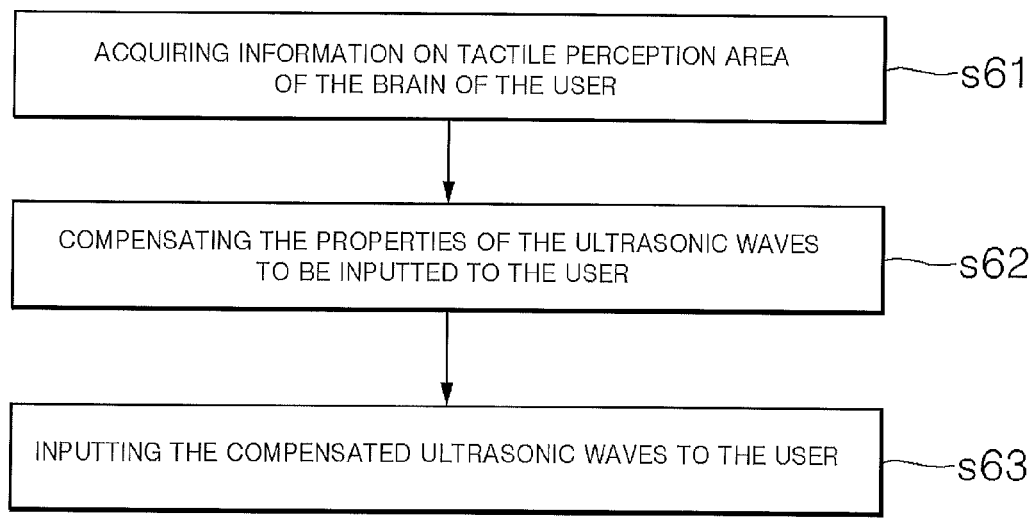
FIG. 6 is a flowchart representing a method for generating the tactile sensation through the non-invasive brain stimulation by using the ultrasonic waves in accordance with the present invention.

FIG. 6 is a flowchart representing a method for generating the tactile sensation through the non-invasive brain stimulation by using the ultrasonic waves in accordance with the present invention.

By referring to FIG. 6, the method for generating a tactile sensation through non-invasive brain stimulation by using ultrasonic waves largely includes a step of acquiring information on the range of the tactile perception areas S61, a step of compensating the properties of the ultrasonic waves S62, and a step of projecting the compensated ultrasonic waves to the user S63.

At step S61, information required to non-invasively stimulate a specific part of the brain of the specified user through one or multiple ultrasonic transducer units included in the ultrasonic transducer module must be obtained, and this is a step of basically obtaining the information on the range of the tactile perception areas in the brain of the user.

At step S61, the information on the range of the tactile perception areas in the brain of the specified user is acquired by referring to the first tactile perception location in the tactile perception areas in the brain that perceives the stimulation to the first body of the specified user, if being inputted, and the second tactile perception location in the tactile perception areas in the brain that perceives the stimulation to the second body of the specified user, if being inputted. As explained by referring to FIGS. 1 and 5 above, because individual persons have different brain sizes and different locations and sizes of the tactile perception areas, the locations of cortical areas that show the responses to tactile stimulation are slightly different. Accordingly, the initial location of the transducer module becomes adjusted by observing the brain activity responding to the stimulation to two body parts of the user (e.g., two fingertips or two tiptoes). Additionally, the information on the range of the tactile perception areas in the brain by respective body parts is obtained by using the information detected by the brain activity monitoring sensor 123 through the calibration, i.e., normalization to the full length (or size) of the tactile areas of the cortex. Through these, stimulation locations of the body parts may be adjusted minutely. As one example, as illustrated in FIG. 5, after stimulation is given by facing the big thumbs and small fingers of both hands with each other to press or touch each other or by tapping the thumb and the small finger repeatedly on a hard place such as a desk, the locations to the stimulation can be detected through the monitoring sensor and the information on the range of the tactile area of the cortex can be obtained by using the information on the detected locations.

At step S62, the properties of the ultrasonic waves to be inputted to the user through the ultrasonic transducer unit are compensated by referring to the information on the range of the tactile perception areas in the brain of the user acquired at step S61. This step S62 is to compensate the properties of the ultrasonic waves to be inputted to the specified user through the ultrasonic transducer unit by referring to the information on the range of the tactile perception areas in the brain of the user acquired at step S61.

At step S63, the generated ultrasonic waves whose properties are compensated at the step S62 is inputted (or projected) to the specified user through the ultrasonic transducer units. Accordingly, if the ultrasonic waves with particular strength are inputted to the specific area of the cortex responding to the tactile stimulation, the user comes to feel the stimulation with various strengths for various senses of touch such as vibration, senses of pressure, texture, and temperature, pain, etc.

As such, according to the apparatus and method for generating the tactile sensation through the non-invasive brain stimulation in accordance with the present invention, the stimulation may be given while the strength, frequency, and interval of the ultrasonic waves are adjusted depending on various senses of touch such as senses of pressure, vibration and temperature, slide, etc. and the user may feel the desired tactile sensation by predicting the reflection and refraction phenomena generated when the ultrasonic waves transmit the skull and stimulating the accurate location.

If the apparatus for generating the tactile sensation through non-invasive brain stimulation in accordance with the present invention is used, the user can interact with it while feeling the senses of touch without losing the sense of immersion in a virtual environment composed of videos, voices, etc. because no separate apparatus is mounted on the hand of the user. Moreover, if an Avatar robot is sent remotely to operate a task, the user can obtain an effect of being able to feel a tactile sensation as if the user operated personally by hand.

The embodiments of the present invention as explained above can be implemented in a form of executable program command through a variety of computer means recordable to computer readable media. The computer readable media may include solely or in combination, program commands, data files and data structures. The program commands recorded to the media may be components specially designed for the present invention or may be usable to a skilled person in a field of computer software. Computer readable record media include hard disk, CD-ROM, DVD, floptical disk, USB flash drive, SSD, Micro SSD, ROM, RAM and flash memory specially designed to store and carry out programs. Program commands include not only a machine language code made by a complier but also a high level code that can be used by an interpreter etc., which is executed by a computer. The aforementioned hardware apparatus can work as more than a software module to perform the action of the present invention and they can do the same in the opposite case.

In accordance with the present invention, to generate various senses of touch such as senses of pressure, vibration, and temperature, slide, etc., users can feel their desired senses of touch because stimulation can be made by adjusting the strength, frequency, and interval of the ultrasonic waves depending on a characteristic by user and the accurate location can be stimulated not only by predicting the reflection and refraction phenomena when the ultrasonic waves pass through the skull of the user but also by considering even the characteristics of the tactile perception areas in the brains of the users.

If the apparatus for generating the tactile sensation through the non-invasive brain stimulation in accordance with the present invention, the user can interact with it while feeling the tactile sensation without losing the sense of immersion in the virtual environment composed of videos or voices because no separate apparatus is not mounted on the hand of the user. Besides, if the Avatar robot is sent remotely to operate a task, the effect of the user feeling the tactile sensation can be obtained as if the user operated directly by hand.

What is claimed is:

1. An apparatus for creating a tactile sensation through non-invasive brain stimulation by using ultrasonic waves, comprising:
   at least one support fixture configured to fix the apparatus to a head of a specified user;
   a brain activity monitoring sensor supported by the at least one support fixture, said brain activity monitoring sensor configured to acquire information on a range of tactile perception areas in the brain of the specified user;
   at least one processor in electronic communication with the brain activity monitoring sensor, said processor configured to determine at least one compensating value for ultrasonic waves to be inputted to the specified user through at least one ultrasonic transducer unit based on the acquired information on the range of tactile perception areas in the brain of the specified user;
   said at least one processor further configured to determine properties of ultrasonic waves to be inputted to the specified user through the at least one ultrasonic transducer unit by referring to the compensating value; and
   said at least one ultrasonic transducer unit supported by the at least one support fixture and in electronic communication with said at least one processor to receive said properties of said ultrasonic waves, said ultrasonic transducer unit configured to generate and input the ultrasonic waves having said properties into the brain of the specified user, resulting in the tactile sensation within the brain of the specified user non-invasively;
   wherein the brain activity monitoring sensor acquires the information on the range of the tactile perception areas in the brain of the specified user by referring to a first tactile perception location in the tactile perception areas in the brain that perceives stimulation to a first body part of the specified user, when inputted, and a second tactile perception location in the tactile perception areas that perceives stimulation to a second body part, when inputted and said processor determines properties of the ultrasonic waves to be inputted to the specified user through the ultrasonic transducer unit by referring to the acquired information on the range of the tactile perception areas in the brain of the specified user.

2. The apparatus of claim 1, wherein the processor determines the compensating value for the ultrasonic waves to be inputted to the specified user through the ultrasonic transducer unit by referring to a path from the first tactile perception location to the second tactile perception location along the tactile perception areas in the brain of the specified user.

3. The apparatus of claim 1, wherein the first body part is a first finger of one hand of the specified user and the second body part is a second finger thereof.

4. The apparatus of claim 1, wherein the processor, based on information from the brain activity monitoring sensor, additionally adjusts a physical location of the ultrasonic transducer unit on the brain of the specified user to adjust the location of the brain of the specified user on which the ultrasonic waves are focused.

5. The apparatus of claim 1, wherein:
   the brain activity monitoring sensor acquires information on a range of a specific tactile perception area, among all the tactile perception areas, in the brain of the specified user used to feel a certain tactile sensation or deciding an accurate range of the tactile perception areas in the brain at a present status by monitoring the size of a brain which is changed depending on an emotion and a mental state of the specified user; and the processor adjusts a location of a focal point of the ultrasonic transducer unit which is focused on the brain of the specified user by referring to the information on the range of the specific tactile perception areas and the size of the brain at the present status acquired through the brain activity monitoring sensor.

6. The apparatus of claim 5, wherein the processor adjusts a location on the brain of the specified user on which the ultrasonic waves are focused at a state with three degrees of freedom.

7. The apparatus of claim 6, wherein the processor adjusts the three degrees of freedom with software or adjusts two thereof with hardware, and the other with software.

8. The apparatus of claim 7, wherein at least some of strengths, frequencies, and phase differences of the ultrasonic waves inputted to the specified user through the ultrasonic transducer unit are adjusted with software, and the physical location of the ultrasonic transducer unit on the brain of the specified user is adjusted with hardware.

9. The apparatus of claim 1, wherein the processor further determines properties of the ultrasonic waves to be inputted to the specified user based on at least some of thickness of the skull of the brain of the specific user and that of skin or internal fat layer thereof.

10. The apparatus of claim 9, wherein the processor further determines properties of the ultrasonic waves to be inputted by referring to transmission properties of the ultrasonic waves including reflection and/or refraction attributes of the skull of the brain of the specified user.

11. The apparatus of claim 10, further comprising:

a brain map database stored in an electronic memory for recording information on locations on the brain to be stimulated to transmit various senses of touch and the properties of the ultrasonic waves to transmit the senses of touch, and wherein the processor decides data recorded in the brain map database as a reference value and determines the properties of the ultrasonic waves to be inputted to the specified user through the ultrasonic transducer unit by referring to transmission characteristics of the ultrasonic waves including the reflection and/or refraction of the skull of the brain of the specified user.

12. The apparatus of claim 11, wherein the properties of the ultrasonic waves to transmit the senses of touch recorded in the brain map database include at least some of strengths, frequencies, and phases of the ultrasonic waves.

13. The apparatus of claim 1, wherein the at least one ultrasonic transducer unit includes a transducer array composed of multiple transducer units.

14. The apparatus of claim 1, wherein the ultrasonic transducer unit inputs the ultrasonic waves to the brain of the specified user through a medium for transmitting the ultrasonic waves.

\* \* \* \* \*